United States Patent [19]

Mederski et al.

[11] Patent Number: 5,371,226
[45] Date of Patent: Dec. 6, 1994

[54] 2-OXOQUINOLINE DERIVATIVES

[75] Inventors: Werner Mederski, Erzhausen; Dieter Dorsch, Ober-Ramstadt; Norbert Beier, Reinheim; Ingeborg Lues, Darmstadt; Klaus-Otto Minck, Ober-Ramstadt; Pierre Schelling, Muhltal, all of Germany

[73] Assignee: Merck Patent Gesellschaft Mit Beschrankter Haftung, Darmstadt, Germany

[21] Appl. No.: 31,977

[22] Filed: Mar. 16, 1993

[30] Foreign Application Priority Data

Mar. 16, 1992 [DE] Germany .............................. 4208304

[51] Int. Cl.$^5$ ................ C07D 215/48; C07D 215/227; C07D 215/50; A61K 31/47
[52] U.S. Cl. .................................... 546/156; 546/157; 546/158
[58] Field of Search ........................ 546/156, 157, 158; 514/312

[56] References Cited

U.S. PATENT DOCUMENTS

| | | | |
|---|---|---|---|
| 4,880,804 | 11/1989 | Carini et al. | 514/16 |
| 5,036,048 | 7/1991 | Watkins | 514/234.5 |
| 5,283,241 | 2/1994 | Bochis et al. | 514/183 |
| 5,284,841 | 2/1994 | Chu et al. | 514/183 |

FOREIGN PATENT DOCUMENTS

| | | |
|---|---|---|
| 187322A1 | 7/1986 | European Pat. Off. |
| 0400974 | 12/1990 | European Pat. Off. |
| 411766A1 | 2/1991 | European Pat. Off. |
| 419048A2 | 3/1991 | European Pat. Off. |
| 0430709 | 6/1991 | European Pat. Off. |
| 487745A1 | 6/1992 | European Pat. Off. |
| 91/14367 | 10/1991 | WIPO |

OTHER PUBLICATIONS

Chem Abstracts 117:251364a, 1992.
Chiu et al., The Journal of Pharmacology and Experimental Therapeutics, vol. 250, No. 3, pp. 867-874 (May 22, 1989).
Wong et al., The Journal of Pharmacology and Experimental Therapeutics, vol. 252, No. 2, pp. 719-725 (Oct. 26, 1989).
Heterocycles, 96:181163f, 1982.
Chemical Abstracts, 97:98357x, 1982.
Heterocycles, 98:34510e, 1983.
Chemical Abstracts, 98:78131m, 1983.
Heterocycles, 100:68187e, 1984.

*Primary Examiner*—C. Warren Ivy
*Assistant Examiner*—D. Margaret M. Mach
*Attorney, Agent, or Firm*—Millen, White, Zelano & Branigan

[57] ABSTRACT 2-oxoquinoline derivative of formula I;

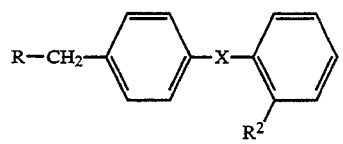

I wherein
R is

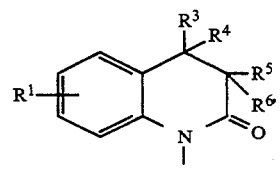

and
$R^1$ to $R^6$ and X are as defined in claim 1, and their salts exhibit antagonistic properties towards angiotensin II and have inter alia a hypotensive action.

5 Claims, No Drawings

2-OXOQUINOLINE DERIVATIVES

SUMMARY OF THE INVETION

The invention relates to novel 2- oxoquinoline derivatives of formula I:

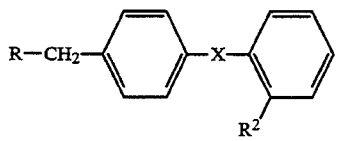

wherein
R is

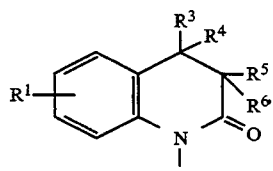

$R^1$ is H, A, OA or SA,
$R^2$ is H, COOH, COOA, CN, $NO_2$, $NH_2$, $NHCOR^7$, $NHSO_2R^7$ or 1H-tetrazol-5-yl,
$R^3$ and $R^4$ are in each case H or A,
$R^5$ and $R^6$ are in each case H, A, COOH, COOA, cyanoalkyl, HOOC-alkyl, ACCO-alkyl, $H_2NCO$-alkyl, ANHCO-alkyl, $A_2NCO$-alkyl, cyanoalkenyl, HOOC-alkenyl, AOOC-alkenyl, 1H-tetrazol-5-ylalkyl, 2-oxo-oxazolidinylalkyl, Ar-alkyl, AO-alkyl, ArO-alkyl, Ar-alkyl-O-alkyl, formylalkyl, oxoalkyl, HOOC-oxoalkyl, AOOC-oxoalkyl, oximinoalkyl, O-alkyloximinoalkyl, HO-alkyl or $R^5R^9N$-alkyl,
$R^3$ and $R^5$ together are also a bond,
$R^7$ is alkyl having 1–6 C atoms, it also being possible for one or more H atom(s) to be replaced with F,
$R^8$ is H or A,
$R^9$ is H, A, A—CO, Ar—CO, COOA, $CONH_2$, CONHA, CONHAr, $CON(A)_2$ or CONAAr,
X is absent or is —NH—CO—, —CO—NH—, —O—CH(COOH)—, —NH—CH(COOH)—, —NA—CH(COOH)—, —CH=C(COOH)—, —CH=C(CN)—or —CH=C(1H-tetrazol-5-yl)—,
A is alkyl having 1–6 C atoms,
Ar is a phenyl group which is unsubstituted or monosubstituted by $R^7$, $OR^7$, Hal, COOH, COOA, CN, $NO_2$, $NH_2$, NHA, $N(A)_2$, $NHCOR^7$, $NHDO_2R^7$ or 1H-tetrazol-5yl, and
Hal is F, Cl, Br or I, and
wherein the "alkyl" moiety or "alkenyl" moiety of said groups contains up to 6 C atoms in each case, and their salts.

An object of the invention was to find novel compounds with valuable properties, especially compounds which can be used for the preparation of drugs.

It has been found that the compounds of formula I and their salts possess very valuable pharmacological properties coupled with a good tolerance by hosts. In particular, they exhibit antagonistic properties towards angiotensin II and can therefore be used for the treatment of angiotensin II-dependent hypertension, aldosteronism and cardiac insufficiency, as well as disorders of the central nervous system. These effects can be determined by conventional in vitro or in vivo methods such as those described for example in U.S. Pat. No. 4,880,804 and in WO 91/14367, as well as those described by A. T. Chiu et. al., J. Pharmacol. Exp. Therap. 250, 867–874 (1989), and by P. C. Wong et. al., ibid. 252, 719–725 (1990; in vivo, on rats).

The compounds of formula I can be used as pharmaceutical active ingredients in human and veterinary medicine, especially for the prophylaxis and/or therapy of cardiac, circulatory and vascular diseases and in particular of hypertonia, cardiac insufficiency and hyperaldosteronism, furthermore of hypertrophy and hyperplasy of the blood vessels and the heart, angina pectoris, cardiac infarction, haemorrhagic stroke, restenosis after angioplaty or by-pass surgery, arteriosclerosis, ocular hypertension, glaucoma, macular degeneration, hyperuricaemia, disturbances of the renal functions such as renal failure, diabetic complications such as nephropathia diabetica or retinopathia diabetica, psoriasis, angiotensinII-induced disturbances in female sexual organs, cognitive disorders, f.e. dementia, amnesia, disturbances of the function of memory, states of fear, depressions and/or epilepsy.

The invention relates to the compounds of formula I and their salts and to a process for the preparation of these compounds and their salts, characterised in that
(a) a compound of formula II:

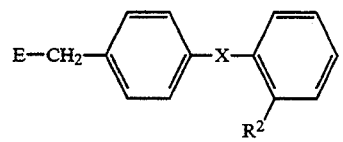

wherein
E is Cl, Br, I, a free OH group or an OH group which has been functionally modified to acquire reactivity, and
$R^2$ and X are as defined in claim 1,
is reacted with a compound of formula III:

H—R    III wherein
R is as defined in claim 1,
or
(b) to prepare a compound of formula I wherein X is —NH—CO— or —CO—NH—, a compound of formula IV:

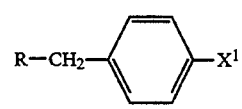

wherein
$X^1$ is $NH_2$ or COOH, and
R is as defined in claim 1,
or a reactive derivative of this compound, is reacted with a compound of formula V:

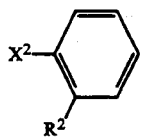

V whererin
X² is COOH (if X¹ is NH₂) or NH₂ (if X¹ is COOH), and
R² is as defined in claim 1,
or with a reactive derivative of this compound, or
(c) a compound of formula I is freed from one of its functional derivatives by treatment with a solvolysing or hydrogenolysing agent,
and/or one or more radicals R and/or F² in a compound of formula I are converted to one or more other radicals R and/or F², and/or a base or acid of formula I is converted to one of its salts.

Above and below, the radicals or parameters R, R¹ to R⁹, X, A, Ar, Hal, E, X¹ and X² are as defined in formulae I, II, IV and V, unless expressly indicated otherwise.

In the above formulae, A has 1–6, preferably 1, 2, 3 or 4 C atoms. A is preferably methyl, or else ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3or 4-methylpentyl, 1,1-, 1,2-, 1,3-, 2,2-, 2,3- or 3,3-dimethylbutyl, 1- or 2-ethylbutyl, 1-ethyl-1-methyl-propyl, 1-ethyl-2-methylpropyl or 1,1,2- or 1,2,2-tri-methylpropyl. Accordingly, the radical OA is preferably methoxy, or else ethoxy, propoxy, isopropoxy, butoxy, isobutoxy, sec-butoxy or tert-butoxy, and the radical SA is preferably methylthio, or else ethylthio, propylthio, isoporpylthio, butylthio, isobutylthio, sec-butylthio or tert-butylthio.

Hal is preferably F, Cl or Br, or else I.

The radical Ar is preferably an unsubstituted phynyl group, or else preferably a phenyl group substituted in the o-position or substituted in the m- or p-position. Preferred substituents are COOH, COOA, NO₂, NH₂ and N(A)₂. Accordingly, Ar is preferably phenyl, (especially) o-, m- or p-carboxyphenyl, (especially) o, m- or p-methoxycarbonylphenyl, (especially) o-, m- or p-ethoxycarbonylphenyl, (especially) o-, m- or p-nitrophenyl, (especially) o-, m- or p-aminophenyl, (especially) o-, m-or p-dimethylaminophenyl, (especially) o-, m- or p-diethylaminophenyl, or else preferably o-, m-or p-tolyl, o-, m- or p-trifluoromethylphenyl, o-, m- or p-methoxyphenyl, o-, m- or p-fluorophenyl, o-, m- or p-iodophenyl, o-, m- or p-cyanophenyl, o-, m- or p-methylaminophenyl, o-, m- or p-acetamidophenyl, o-, m-or p-trifluoroacetamidophenyl, o-, m- or p-methylsufonamidophenyl, o-, m- or p-trifluoromethylsulfonamidophenyl or o-, m- or p-(1H-tetrazol-5-yl)phenyl.

R is a radical derived from 1,2-dihydroquinoline or a radical derived form 1,2,3,4-tetrahydroquinoline or, more precisely:

(a) 1,2-dihydro-2-oxo-3-R⁶-4R⁴-5(or 6 or 7 or 8)-R¹-quinolyl (if R³ and R⁵ together are a bond), or
(b) 1,2,3,4-tetrahydro-2oxo-3-R⁵-3-R⁶-4-R³-4-R⁴-5-(or 6 or 7 or 8 )-R¹-quinolyl (if R³ and R⁵ separately are in each case one of the radicals indicated).

Accordingly, the compounds of formula I include those of formulae Ia and Ib, wherein R is as defined in each case under (a) or (b). The compounds of formula Ia are preferred.

The radical R¹ is preferably H or A, especially methyl or ethyl.

A radical R¹ other than H is preferably located in the 7- or 8-position of the quinoline ring.

The radical R² is preferably CN, or else preferably 1H-tetrazol-5-yl, COOH, COOOCH₃, COOC₂H₅ or NHSO₂CF₃.

The radicals R³ and R⁴ are in each case preferably H or methyl. Furthermore, R³ and R⁵ together are preferably a bond.

One of the radicals R⁵ and R⁶ is preferably H; the other is preferably also H or A (especiall CH₃), COOH, COOA (especially methoxycarbonyl, ethoxycarbonyl), cyanoalkyl (especially cyanomethyl, 2-cyanoethyl, 3-cyanopropyl), carboxyalkyl (especially carboxymethyl, 2- carboxyethyl, 3-carboxypropyl), AOOC-alkyl (especially methoxycarbonylmethyl, ethoxycarbonymethyl, 2-methoxycarbonylethyl, 2-ethoxycarbonylethyl), carbamoyl-alkyl (especially carbamoylmethyl, 2-carbamoylethyl), N-alkylcarbamoylalkyl [especially N-methylcarbamoylmethyl, N-ethylcarbamoylmethyl, 2-(N-methylcarbamoyl)ethyl, 2-(N-ethylcarbamoyl)ethyl], N,N-dialkylcarbamoylalkyl [especially N,N-dimethylcarbamoylmethyl, N,N-diethylcarbamoylmethyl, 2-(N,N-dimethylcarbamoyl)ethyl, 2-(N,N-diethylcarbamoyl)ethyl], cyanoalkenyl (especially 3-cyanoprop-2-en-1-yl), carboxyalkenyl (especially 3-carboxyprop-2-en-1-yl), alkoxycarbonylalkenyl (especially 3-methoxycarbonylprop-2-en-1-yl, 3-ethoxycarbonylprop-2-en-1-yl), 1H-tetrazol-5-ylalkyl [especially 1H-tetrazol-5-ylmethyl, 2--(1H-tetrazol-5yl)ethyl, 3-(1H-tetrazol-5-y1)propyl], 2-oxooxazolidinylalkyl [especially 2-oxooxazolidinylmethyl, 2-(2-oxooxazolidinyl)ethyl], Ar-alkyl [especially benzyl, 1- or 2-phenylethyl, 1-, 2- or 3-phenylpropyl, 1-, 2-, 3- or 4-phenylbutyl, o- , m- or p-fluorobenzyl, (preferably) o-, m- or p-chlorobenzyl, o, m- or p-bromobenzyl, o-, m- or p-methylbenzyl, o-, m- or p-trifluoromethylbenzyl, o-, m- or p-methoxycarbonylbenzyl, o-, m- or p-ethoxycarbonylbenzyl, 9preferably) o-, m- or p-cyanobenzyl, o-, m- or p-carboxybenzyl, o-, m- or p-nitrobenzyl, (preferably) o-, m- or p-aminobenzyl, o-, m- or p-dimethylaminobenzyl, (preferably) o-, m- or p-(1H-tetrazol-50yl)benzyl], alkoxyalkyl (especially methoxymethyl, ethoxymethyl, 2-methoxyethyl, 2-ethoxyethyl), Ar-oxyalkyl (especially phenoxymethyl, 2-phenoxyethyl), Ar-alkyloxyalkyl (especially benzyloxymethyl, 2-benzyloxyethyl), formylalkyl (especially formylmethyl, 2-formylethyl), oxoalkyl (especially 2-oxopropyl, 2- or 3-oxobutyl, 3,3-dimethyl-2-oxobutyl), carboxyoxoalkyl (especially 2-carboxy-2-oxobutyl), carboxyoxoalkyl (especially 2-carboxy-2-oxoethyl), alkoxycarbonyloxoalkyl (especially 2-methoxycarbonyl-2-oxoethyl, 2-ethoxycarbonyl-2-oxoethyl), oxoethyl), oximinoalkyl (especially 2-oximinopropyl, 2- or 3-oximinobutyl, 3,3-dimethyl-2-oximinobutyl), O-alkyloximinoalkyl [especially 2-(O-methyloximino)propyl, 2-(O-ethyloximino)propyl, 2- or 3-(O-methyloximino)butyl, 3,3-dimethyl-2-(O-methyloximino)butyl], hydroxyalkyl (especially hydroxymethyl, 2-hydroxyethyl), aminoalkyl (especially aminomethyl, 2-aminoethyl), alkylaminoalkyl (especially methylaminomethyl, ethylaminomethyl, 2-methylaminoethyl, 2-ethylaminoethyl), dialkylaminoalkyl (especially dimethylaminomethyl, diethylaminomethyl, 2-dimethylaminoethyl, 2-diethylaminoethyl), alkanoylaminoalkyl (espcially acetamidomethyl, propionamidomethyl, 2-acetamidoethyl), aroylaminoalkyl (especially benzamidomethyl, 2-benzamidoethyl), alkoxycarbonylaminoalkyl (especially methoxycarbonylaminomethyl, ethoxycarbonylaminomethyl, 2-methoxycarbonylaminoethyl, 2-ethoxycarbonylaminoethyl), ureidoalkyl (especially ureidomethyl, 2-ureidoethyl), N-alkylureidoalkyl (especially N-methylureidomethyl, N-ethylureidomethyl, 2-N-methylureidoethyl, 2-N-ethylureidoethyl), N,N-dialkylureidoalkyl (especially N,N-dimethylureidomethyl, N,N-diethylureidoethyl, 2-N,N-dimethylureidoethyl, 2-N,N-diethylureidoethyl), N-Ar-ureidoalkyl (especially N- phenylureidomethyl, 2-N-phenylureidoethyl) or N-alkyl-N-Ar-ureidoalkyl (especially N-methyl-N-phenylureidomethyl, N-ethyl-N-phenylureidomethyl).

The radical $R^7$ is preferably trifuuoromethyl, or else preferably A, such as methyl or ethyl, or else fouoromethyl, difluoromethyl, pentafluoroethyl or heptafluoropropyl. The amount of F atoms replacing H atoms may be from 1 or perfluoro.

The radical $R^8$ is preferably H, or else preferably methyl or ethyl.

The radical $R^9$ is preferably H, A (espcieally methyl or ethyl) or A—CO (espcially acetamido).

The radical X is preferably absent.

The "alkyl" moiety of said groups is preferably —$CH_2$— or —$CH_2CH_2$—, or else preferably —CH($CH_3$)—, —($CH_2$)$_3$—, —($CH_2$)$_4$—, —($CH_2$)$_5$— or —($CH_2$)$_6$—, and the "alkenyl" moiety is preferably —$CH_2$—CH=CH—.

The compounds of formula I can possess one or more chiral centers and can therefore exist in different forms (optically active or optically inactive). Formula I includes all these forms.

Accordingly, the invention relates especially to those compounds of formula I in which at least one of said radicals has one of the preferred meanings indicated above. Some preferred groups of compounds can be expressed by the following partial formulae Ic, Id, Ie, Iac, Iad, Iae, Ibc, Ibd, Ibe, Icd, Ice, Ide, Iacd, Ibcd, Iace, Ibce, Iade, Ibde, Icde, Iacde and Ibcde, which correspond to formulae I and Ia and Ib and wherein the radicals not described more precisely are as defined in formulae I and Ia and Ib:

compounds of formulae Ic and Iac and Ibc, which correspond to formulae I and Ia and Ib except that in addition $R^1$ is H, methyl or ethyl therein;
compounds of formulae Id and Iad, Ibd, Icd, Iacd and Ibcd, which correspond to formulae I and Ia, Ib, Ic, Iac and Ibc except that in addition $R^2$ is CN or (preferably) 1H-tetrazol-5-yl therein; and
compounds of formulae Ie and Iae, Ibe, Ice, Ide, Iace, Ibce, Iade, Ibde, Icde, Iacde and Ibcde, which correspond to formulae I, Ia, Ib, Ic, Id, Iac, Ibc, Iad, Ibd, Icd, Iacd and Ibcd except that in addition $R^3$ is H or $CH_3$ and $R^4$ is H therein.

The compounds of formula I and also the starting materials for their perparation are moreover prepared by methods known per se, such as those described in the literature (for example in the standard works like Houben-Weyl, Methoden der organischen Chemie (methods of Organic Chemistry), Georg-Thieme-Verlag, Stuttgart, but especially in European patent application A2-0 430 709 and U.S. Pat. No. 4,880,804), under reaction conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III.

In the compounds of formula II, E is preferably Cl, Br, I or an OH group which has been functionally modified to acquire reactivity, such as alkylsulfonyloxy having 1–6 C atoms (preferably methylsulfonyloxy) or arylsulfonyloxy having 6–10 C atoms (preferably phenyl-or p-tolyl-sulfonyloxy).

The reaction of II with III is conveniently carried out by first converting III to a salt by treatment with a base, for example with an alkali metal alcoholate such as $CH_3ONa$ or potassium tert-butylate in an alcohol such as $CH_3OH$ or in an amide such as dimethyl-formamide (DMF), or with an alkali metal hydrde such as NaH or an alkali metal alcoholate in DMF, and then reacting said salt with II in an inert solvent, for example an amide such as DMF or dimethylacetamide, or a sulfoxide such as dimethyl sulfoxide (DMSO), conveniently at temperatures of between —20° and 100°, preferably of between 10 ° and 30°. Other suitable bases are alkali metal carbonates such as $Na_2CO_3$ or $K_2CO_3$, or alkali metal hydrogen carbonates such as $NaHCO_3$ or $KHCO_3$.

Some of the starting materials, especially those of formula III, are known. If they are not known, they can be prepared by known methods analogously to known substances.

Acid amides of formula I (X=—NH—CO— or —CO—NH—) can also be obtained by reaction of compounds of formula IV (or reactive derivatives thereof) with compounds of formula V (or reactive derivatives thereof).

Suitable reactive derivatives of the carboxylic acids of formulae IV and V ($X^1$ or $X^2$=COOH) are advantageously the corresponding chlorides, bromides or anhydrides. The reaction is conveniently carried out in the presence of an inert solvent, for example a halogenated hydrocarbon such as methylene chloride, chloroform, trichloroethane of 1,2-dichloroethane, or an ether such as tetrahydrofuran (THF) or dioxane, at temperatures of between 0° and 150° , preferably of between 20° and 20°. If acid halides are reacted, it is recommended to add a base, for example a tertiary amine such as triethylamine, pyridine or 4-dimethylaminopyridine.

A compound of formula I can also be freed from one of its functional derivatives by treatment with a colvolysing (for example hydrolysing) or hydrogenolysing agent.

Thus it is possible, using one of the methods indicated, to prepare a compound which has formula I but in which a etraxol-5-yl group is replaced with a tetraxol-5-yl group functionally modified in the 1-positioin (protected by a protecting group). Examples of suitable protecting groups are : triphenylmethyl, which can be cleaved with HCl or formic acid in an inert solvent or solvent mixture, for example methanol or ether/methylene chloride/methanol; 2-cyanoethyl, which can be cleaved with NaOH in water/THF; and p-nitrobenzyl, which can be cleaved with $H_2$/Raney nickel in ethanol (compare European patent applicatoin A2-0 291 969).

It is also possible to convert one compound of formula I to another compound of formula I by converting one of more of the radicals R and/or $R^2$ to other radicals R and/or $R^2$, for example by reducing nitro groups to amino groups (for example by hydrogenation on Raney nickel or Pd-on-charcoal in an inert solvent such as methanol or ethalol), and/or functiaonally modifying free amino and/or hydroxyl groups, and/or freeing functionally modified amino and/or hydroxyl groups by solvolysis or hydrogenolysis, and/or replacing halogen atoms with CN groups (for example by reaction with copper(I) cyanide), and/or hydrolysing nitrile groups to COOH groups, or converting nitrile groups to tetrazolyl groups with hydrazoic acid derivatives, for example sodium axide in N-methyl-pyrrolidone or trimethyltin azide in toluene.

Thus, for example, free amino groups can be acylated in conventional manner with an acid chloride or anhydride, or free hydroxyl and/or NH groups can be alkylated with an unsubstituted or substituted alkyl or Aralkyl halide or with aldehydes such as formaldehyde, in the presence of a reducing agent such as $NaBH_4$ or formic acid, conveniently in an inert solvent such as methylene chloride or THF and/or in the presence of a base such as triethylamine or pyridine, at temperatures of between $-60°$ and $+30°$.

If desired, a functionally modified amino and/or hydroxyl group in a compound of formula I can be freed by solvolysis or hydrogenolysis using conventional methods. Thus, for example, a compound of formula I containing an $NHCOR^7$ or COOA group can be converted to the correspding compound of formula I containing an $NH_2$ or COOH group instead. Ester groups can be saponified for example with NaOH or KOH in water, water/THF or water/dioxane, at temperatures of between $0°$ and $100°$.

The reaction of nitriles of formula I ($R^2$=CN or $R^5$ or $R^6$ =cyanoalkyl) with hydrazoic acid derivatives leads to tetrazoles of formula I ($R^2$ =1H-tetrazol-5-yl and/or $R^5$ or $R^6$ = 1H-tetraxol-5-ylalkyl). It is preferable to use trialkyltin axides such as trimethyltin azide, in an inert solvent, for example an aromatic hydrocarbon such as toluene, at temperatures of between $20°$ and $150°$, preferably of between $80°$ and $140°$, or sodium azide in N-methylpyrrolidone at temperatures of between about $100°$ and $200°$.

It is further possible to convert a ketone of formula I ($R^5$ and/or $R^6$=for example oxoalkyl) to the correspdong oxime or O-alkyloxime by reaction with hydroxylamine or O-alkylhydroxylamie, conveniently in an inert solvent at $10°-30°$.

A base of formula I can be converted with an acid to the corresponding acid additional salt. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphoric acids such as orthophosphoric acid, and sulfamic acid, as well as organic acids, especially aliphatic, alicyclic, araliphatic, aromatic or heterocyclic monobasic or polybasic arboxylic, sulfonic or sulfurica acids, for example formic acid, acetic acid, propionic acid, pivalic acid, diethylacetic acid, malonic acid, succinic acid, pimelic acid, fumaric acid, jmaleic acid, lactic acid, tartaric acid, malic acid, citric acid, gluoconic acid, ascorbic acid, nicotinic acid, isonicotinic acid, methane- or ethane-sulfonic acid, ethanedisulfonic adic, 2-hydroxyethanesulfonic acid, benzenesulfonic acid, p-toluenesulfonic acid, naphthalneemonosulfonic and -disulfonic acids and laurylfulfuric acid. Salts with physiologically unacceptable acids, for example picrates, can be used for isolationg and/or purifying the compounds of formula I.

On the other hand, compounds of formula I containing COOH or tetrazolyl groups can be converted with bases (for example sodium or potassium hydroxide or carbonate) to the corresponding metal salts, especially alkali metal or alkaline earth metal salts, or to the corresponding ammonijm salts. The potassium salts of the tetrazolyl derivatives are particularly preferred.

The novel compounds of formula I and their physiologically acceptable salts can be used for the preparation of pharmaceutical formulations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compunds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant or prepellant mixture (for example hydrocarbons such as propane of butane, or fluorocarbons such as heptafluoropropane). It is convenient here to use the acitve ingredient in micronised form, it being possible for one or more additional physiciologically compatible solvents, for example ethanol, to be present. Inhalation solutions can be administered with the aid of conventional inhalers. The novel compounds can also be lyophilised and the resulting lyophilisates used for example for the manufacture of injectable preparations. The indicated formulations can be sterilised and/or can contain adjuncts such as preservatives, stabilisers and/or wetting agents, emulsifiers, salts for influencing the osmotic pressure, buffer substances and colours and/or flavourings. If desired, they can also contain one or more other active ingredients, for example one or more vitamins, diuretics or antiphlogistics.

The substances according to the invention are normally administered analogously to other known, commercially available preparations, but in particular analogously to the compounds described in U.S. Pat. No. 4,880.804, preferably in doses of between about 1 mg and 1 g, especially of between 50 and 500 mg per dosage unit. The daily dose is preferably between about 0.1 and 100 mg/kg, especially between 1 and 50 mg/kg of body weight. However, the particular dose for each individual patient depends of a very wide variety of factors, for example on the efficacy of the particular compound used, age, body weight, general state of health, sex, diet, time and mode of administration, rate of excretion, drug combination and severity of the particular disease to which the therapy is applied. Oral administration is preferred.

Without further elaboration, it is believed that one skilled in the art can, using the preceding description, utilize the present invetion to its fullest extent. The preferred specific embodiments are, therefore, to be construed as merely illustrative, and not limitative of the disclosure in any way whatsoever.

The entire disclosure of all applications, patents and publications, cited above and below, and of corresponding German No. P 42 08 304.4, are hereby incorporated by reference.

In the following Examples, "conventional working-up" means: Water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization. Rf=Rf on silica gel (by thin layer chromatography; eluent: ethyl acetate/hexane 9:1).

EXAMPLES

Example 1

(a) 12.5 g of potassium tert-butoxide are added at 20° to a solution of 20.3g or 7-ethyl-1,2,3,4-tetrahydro-4,4-dimethyl-2-oxoquinoline [mip. 120°; obtainable by reaction of m-ethylaniline with 3,3-dimethylacryloyl chloride in toluene/methylene chloride to give N-(3,3-dimethylacryloyl)-m-ethylaniline (m.p. 90°) and cyclisation with AlCl3 at 60°-100°]in 700 ml of DMF. The mixure is stirred for 45 minutes, a solution of 30.5g of 4-bromomethyl-2′-cyanobiphenyl in 300 ml of DMF is then added dropwise and the mixture is stirred overnight, evaporated and worked up in conventional manner to give 1-(2′-cyanobiphenyl-4-ylmethyl)-7-ethyl-1,2,3,4-tetrahydro-4,4-dimethyl-2-oxoquinol ine, m.p. 171°–172°.

The following 1-(2′-cyanobiphenyl-4-ylmethyl)-2-oxoquinolines are obtained analogously:

from 1,2-dihydro-2-oxoquinoline (m.p. 198°): 1,2-dihydro-, m.p. 175°;
from 1,2,3,4-tetrahydro-2-oxoquinoline (m.p. 168°): 1,2,3,4-tetrahydro-,m.p. 97°;
from 1,2,3,4-tetrahydro-4,4-dimethyl-2-oxoquinoline (m.p. 114°–115°): 1,2,3,4-tetrahydro-4,4-dimethyl-, m.p. 139°;
from 7-ethyl-1,2-dihydro-4-methyl-2oxoquinoline [m.p. 180°; obtainable by reacxtoin of 3-ethylaniline with 2,2,6-trimethyl-1,3-dioxin-4-one at 120° to govem 3-ethyl-N-(3-oxobutyryl)aniline (Rf 0.52) and cyclisation with H2SO4 at 20°]: 7-ethyl-1,2-dihydro-4-methyl-;
from 7-ethyl-1,2-dihydro-4-methyl-3-p-nitrobenzyl-2-oxo-quinoline [m.p. 284°; obtainable by reaction of 3-ethyl-N-(3-oxobutyryl)-aniline with p-nitrobenzyl chloride to give 3-ethyl-N-(2-p-nitrobenzyl-3-oxo-butyryl)-aniline and cyclisation]: 7-ethyl-1,2-dihydro-4-methyl-3-p-nitrobenzyl-, m.p. 171°;
from 3,7-diethyl-1,2-dihydro-4-methyl-2-oxo-quinoline: 3,7-diethyl-1,2-dihydro-4-methyl-;
from 3-carboxy-7-ethyl-1,2-dihydro-4-methyl-2-oxoquinoline: 3-carboxy-7-ethyl-1,2-dihydro-4-methyl-;
from 7-ethyl-1,2-dihydro-3-methoxycarbonyl-4-methyl-2-oxo-quinoline: 7-ethyl-1,2-dihydro-3-methoxycarbonyl-4-methyl-;
from 3-cyanomethyl-7-ethyl-1,2-dihydro-40-methyl-2-oxo-quinoline: 3-cyanomethyl-7-ethyl-1,2-dihydro-4-methyl-;
from 3-carboxymethyl-7-ethyl-1,2-dihydro-4-methyl-2-oxo-quinoline: 3-carboxymethyl-7-ethyl-1,2-eihydro-4-methyl-;
from 7-ethyl-1,2-dihydro-3-methoxycarbonylmethyl-4-methyl-2-oxo-quinoline (m.p. 209° ): 7-ethyl-1,2-dihydro-3-methoxycarbonylmethyl-4-methyl-, m.p. 115°;
from 7-ethyl-1,2dihydro-3-carbamoylmethyl-4-methyl-2-oxo-quinoline (m.p. 289°): 7-ethyl-1,2-dihydro-3-carbamoylmethyl-4-methyl-, dihydrate, m.p. 253°;
from 7-ethyl-1,2-dihydro-4-methyl-3-N,N-dimethylcarbamoylmethyl-2-oxo-quinoline (m.p. 232°): 7-ethyl-1,2-dihydro-4methyl-3-N,N-dimethylcarbamoylmethyl-, sesquihydrate, m.p. 193°;
from 7-ethyl-1,2-dihydro-4-methyl-3-N,N,-diethyl-carbamoylmethyl-2-oxo-quinoline (m.p. 228°): 7-ethyl-1,2-dihydro-4-methyl-3-N,N-diethylcarbamoylmethyl-, m.p. 188°;
from 3-(3-carboxy-2-propen-1-yl)-7-ethyl-1,2-dihydro-4-methyl-2-oxo-quinoline: 3-(3-carboxy-2-propen -1-yl)-7-ethyl-1,2-dihydro-4-methyl-;
from 7ethyl-1,2-dihydro-3-(3-methoxycarbonyl-2-propenl-yl)-4-methyl-2-oxo-quinoline: 7-ethyl-1,2-dihydro-3-(3-methoxycarbonyl-2-propenl-yl)-4-methyl-;
from 7-ethyl-1,2-dihydro-4-methyl-2-oxo-3-(1H-5-tetrazolylmethyl)-quinoline: 7-ethyl-1,2-dihydro-4-methyl-3-(1H-5-tetrazolylmethyl)-;
from 7-ethyl-1,2-dihydro-4-methyl-2-oxo-3-(2-oxo-5-oxaxolidinylmethyl)-quinoline: 7-ethyl-1,2-dihydro-4-methyl-3-(2-oxo-5-oxazolidinylmethyl)-;
from 7-ethyl-1,2-dihydro-4-methyl-3-o-nitrobenzyl-2-oxo-quinoline: 7-ethyl-1,2-dihydro-4-methyl-3-o-nitrobenzyl-;
from 7-ethyl-1,2-dihydro-4-methyl-3-m-nitrobenzyl-2-oxo-quinoline: 7-ethyl-1,2-dihydro-4-methyl-3-m-nitrobenzyl-;
from 3-o-carboxybenzyl-7-ethyl-1,2-dihydro-4-methyl-2-oxo-quinoline: 3-o-carboxybenzyl-7-ethyl-1,2-dihydro-4-methyl-;
from 7-ethyl-1,2-dihydro-3-o-methoxycarbonylbenzyl-4-methyl-2-oxo-quinoline: 7-ethyl-1,2-dihydro-3-o-methoxycarbonylbenzyl-4-methyl-;
from 7-ethyl-1,2-dihydro-3-p-methoxycarbonylbenzyl-4-methyl-2-oxo-quinoline (m.p. 236°): 7-ethyl-1,2-dihydro-3-p-methoxycarbonylbenzyl-4-methyl-, trihydrat, m.p. 98°;
from 7-ethyl-1,2-dihydro-4-methyl-3-o-dimethylaminobenzyl-2-oxo-quinoline: 7-ethyl-1,2-dihydro-4-methyl-3-o-dimethylaminobenzyl-;
from 7-ethyl-1,2-dihydro-3-methoxymethyl-4-methyl-2-oxo-quinoline: 7-ethyl-1,2-dihydro-3-methoxymethyl-4-methyl-;
from 3-benzyloxymethyl-7-ethyl-1,2-dihydro-4-methyl-2-oxo-quinoline: 3-benzyloxymethyl-7-ethyl-1,2-dihydro-4-methyl-;
from 7-ethyl-3-formylmethyl-1,2-dihydro-4-methyl-2-oxo-quinoline: 7-ethyl-3-formylmethyl-1,2-dihydro-4-methyl-;

from 7-ethyl-1,2-dihydro-4-methyl-2-oxo-3-(2-oxo-propyl)-quinoline: 7-ethyl-1,2-dihydro-4-methyl-3-(2-oxo-propyl)-;
from 7-ethyl-1,2-dihydro-4-methyl-3-(3,3-dimethyl-2-oxo-butyl)-2-oxo-quinoline: 7-ethyl-1,2-dihydro-4-methyl-3-(3,3-dimethyl-2-oxo-butyl)-;
from 3-)2-carboxy-2-oxo-ethyl)-7-ethyl-1,2-dihydro-4-methyl-2-oxo-quinoline: 3-(2-carboxy-2-oxo-ethyl)-7-ethyl-1,2-dihydro-4-methyl-;
from 3-(2-ethoxycarbonyl-2-oxo-ethyl)-7-ethyl-1,2-dihydro-4-methyl-2-oxo-quinoline: 3-(2-ethoxycarbonyl-2-oxo-ethyl)-7-ethyl-1,2-dihydro-4-methyl-;
from 7-ethyl-1,2-dihydro-4-methyl-3-(2-oximino-propyl)-2-oxo-quinoline: 7-ethyl-1,2-dihydro-4-methyl-3-(2-oximinopropyl)-;
from 7-ethyl-1,2-dihydro-4-methyl-3-(3,3-dimethyl-2-oximino-butyl)-2-oxo-quinoline: 7-ethyl-1,2-dihydro-40-methyl-3-(3,3-dimethyl-2-oximino-butyl)-;
from 7-ethyl-1,2-dihydro-4-methyl-3-(2-O-methyl-oximino-porpyl)-2-oxo-quinoline: 7-ethyl-1,2-dihydro-4-methyl-3-(2-O-methyl-oximino-propyl)-;
from 7-ethyl-1,2-dihydro-4-methyl-3-(3,3-dimethyl-2-O-methyl-oximino-butyl)-2-oxo-quinoline: 7-ethyl-1,2-dihydro-4-methyl-3-(3,3-dimethyl-2-O-methyl-oximino-butyl)-;
from 7-ethyl-1,2-dihydro-3-hydroxymethyl-4-methyl-2-oxo-quinoline: 7-ethyl-1,2-dihydro-3-hydroxymethyl-4-methyl-.

b) A mixture of 3.94g of the compound obtained according to (a), 20.6 g of trimethylin azide and 200 ml of toluene is boiled for 24 hours and then evaporated. The residue is taken up in 100 ml of methanolic HCl and the mixture is stirred for 2 hours at 20°, evaporated and worked up in conventional manner to give 7-ethyl-1,2,3,4-tetrahydro-4,4-dimethyl-2-oxo-1-[2'-(1H-5tetrazolyl)-biphenylyl-4-methyl]-quinoline, trihydrate, m.p. 200°.

The following 2-oxo-1-oxo-1-[2'(1H-5-tetrazolyl-biphenylyl-4-methyl]-quinolines are obtained analogously from the cyano compounds mentioned above under a) with trimethyltin azide:
1,2-dihydro-, m.p. 265°
1,2,3,4-tetrahydro-, m.p. 236°
1,2,3,4,-tetrahydro-4,4-dimethyl-, m.p. 176°
7-ethyl-1,2-dihydro-4-methyl-, m.p. 260°
7-ethyl-1,2-dihydro-4-methyl-3-p-nitrobenzyl-, tetrahydrate, m.p. 229°
3,7-diethyl-1,2-dihydro-4-methyl-
3-carboxy-7-ethyl-1,2-dihydro-4-methyl-
7-ethyl-1,2-dihydro-3-methoxycarbonyl-4-methyl-
3-cyanomethyl-7-ethyl-1,2-dihydro-4-methyl- [with the corresponding 3-(1H-5-tetrazolyl-methyl) compound]
3-carboxymethyl-7-ethyl-1,2-dihydro-4-methyl-, trihydrate, m.p. 262°
7-ethyl-1,2-dihydro-3-methoxycarbonylmethyl-4-methyl-, m.p. 215°
7-ethyl-1,2-dihydro-3-carbamoylmethyl-4-methyl-, m.p. 262°
7-ethyl-1,2dihydro-4-methyl-3-N,N-dimethylcarbamoylmethyl-, tetrahydrate, m.p. 225°
7-ethyl-1,2-dihydro-4-methyl-3-N,N-diethylcarbamoylmethyl, m.p. 165°
3-(3-carboxy-2-propen-1-yl)-7-ethyl-1,2-dihydro-4-methyl-
7-ethyl-1,2dihydro-3-(3-methoxycarbonyl-2-propenyl)-4-methyl-
7-ethyl-1,2-dihydro-4-methyl-3-(1H-5-tetrazolyl-methyl)-
7-ethyl-1,2-dihydro-4-methyl-3-(2-oxo-5-oxazolidinyl-methyl)-
7-ethyl-1,2-dihydro-4-methyl-3-o-nitrobenzyl-
7-ethyl-1,2-dihydro-4-methyl-3-m-nitrobenzyl-
3-o-carboxybenzyl-7-ethyl-1,2-dihydro-4-methyl-
7-ethyl-1,2-dihydro-3-o-methoxycarbonylbenzyl-4-methyl-
7-ethyl-1,2-dihydro-4-methyl-3-o-dimethylaminobenzyl-
7-ethyl-1,2-dihydro-3-methoxymethyl-4-methyl-
3-benzyloxymethyl-7-ethyl-1,2-dihydro-4-methyl-
7-ethyl-3-formylmethyl-1,2-dihydro-4-methyl-
7-ethyl-1,2-dihydro-4-methyl-3-(2-oxo-propyl)-
7-ethyl-1,2-dihydro-4-methyl-3-(3,3-dimethyl-2-oxo-butyl)-
3-(2-carboxy-2-oxo-ethyl)-7-ethyl-1,2-dihydro-4-methyl-
7-ethyl-1,2-dihydro-4-methyl-3-(2-oximinopropyl)-
7-ethyl-1,2-dihydro-4-methyl-3-(3,3-dimethyl-2-oximino-butyl)-
7-ethyl-1,2-dihydro-4-methyl-3-(2-O-methyl-oximino-propyl)-
7-ethyl-1,2-dihydro-4-methyl-3-(3,3-dimethyl-2-O-methyl-oximino-butyl)-
7-ethyl-1,2-dihydro-3-hydroxymethyl-4-methyl-.

Example 2

(a) 7-Ethyl-1,2-dihydro-4-methyl-2-oxo-1-[2'-(2-triphenylmethyl-2H-tetrazol-5-yl)biphenyl-4-ylmethyl]-quinoline, m.p. 165°, is obtained analogously to Example 1 from 7-ethyl-1,2-dihydro-4-methyl-2-oxoquinoline and 4-bromomethyl-2' -(2-tripenylmethyl-2H-tetrazol-5-yl)biphenyl.

(b) The product obtained according to (a) (1 g) is stirred with 10 ml of formic acid and 90 ml of methanol for 2 hours at 50°. The solution obtained is evaporated and worked up in conventional manner to give 7-ethyl-1,2-dihydro-4-methyl-2-oxo-1-]2'-(1H-tetrazol-5-yl) biphenyl-4-ylmethyl]quinoline, m.p. 261°.

Example 3

1-[p-(2Cyano-2-phenylvinyl)benzyl]-7-ethyl-1,2-dihydro-4-methyl-2-oxoquinoline, m.p. 227°, is obtained analogously to Example 1 from 1.87 g of 7-ethyl-1,2-dihydro-4-methyl-2-oxoquinoline and 2.98 g of 3-(p-bromomethylphenyl)-2-phenylacrylonitrile [m.p. 178°; obtainable by condensation of p-tolylaldehyde with phenylacetonitrile to give 2-phenyl-3-p-tolylacrylonitrile (m.p. 61°) and brominatoin with N-bromosuccinimde in methylene chloride].

Example 4

A mixture of 2.52 g of 1-p-aminobenzyl-1,2,3,4-tetrahydro-2-oxoquinoline (obtainbale by reactoin of 1,2,3,4-tetrahydro-2-oxoquinoline with p-nitrobenzyl bromide to give 1,2,3,4-tetrahydro-1-p-nitrobenzyl-2-oxoquinoline and subsequent hydrogenation), 1.48 g of phthalic anhydride and 50 ml of chloroform is stirred for 16 hours at 20°. The 1-[4-(2-carboxybenzamido)benzyl]-1,2,3,4-tetrahydro-2-oxoquinoline which as precipitated out is filtered off.

Example 5

A mixture of 2.52 g of 1-p-aminobenzyl-1,2,3,4-tetrahydro-2-oxoquinoline, 3 ml of triethylamine, 0.5 g of 4-dimethylaminopyridine and 120 ml of methylene chloride is cooled to 5° and a solutoin of 2.88 g of o-trifluoromethanesulfonamidobenzoyl chloride in 20 ml of methylene chloride is added dropwise. The mixture is stirred for a further 16 hours at 20°, evaporated and worked up in conventional manner to give 1,2,3,4-tetrahydro-2-oxo-1-[4-(2-trifluoromethanesulfonamidobenzamido)benzyl]quinoline.

Example 6

A mixture of 2.81 g of 1-p-carboxybenzyl-1,2,3,4-tetrahydro-2-oxoquinoline, 10 g of thionyl chloride and 35 ml of chloroform is boiled for 6 hours and evaporated. The crude acid chloride obtained is freed of thionyl chloride residues by repeated dissolution in toluene and evaporation, and dissolved in 80 ml of THF. This solution is added dropwise to a solution of 1.7 g of anthranilic acid and 0.8 g of NaOH in 100 ml of water and the mixture is stirred for 24 hours and acidified to pH 5 with hydrochloric acid. Conventional working-up gives 1-[p-(2-carboxyanilinocarbonyl)benzyl]-1,2,3,4-tetrahydro-2-oxoquinoline.

Example 7

A mixture of 1 g of 1,2,3,4-tetrahydro-1-[4-(α-methoxycarbonylbenzyloxy)bensyl]-2-oxoqunoline (obtainable by reaction of 1,2,3,4-tetrahydro-2-oxo-quinoline with p-benzyloxybenzyl bromide to give the 1-p-benzyloxybenzyl derivative, hydrogenolysis to give 1-p-hydroxybenzyl-1,2,3,4,-tetrahydro-2-oxoquinoline and etherification with methyl α-bromophenylacetate), 12 ml of 2 N aqueous NaOH solution and 48 ml of ethanol is boiled for 2 hours and then evaporated and worked up in conventional manner (aqueous hydrochloric acid to pH 3/ methylene chloride) to give 1-([4-(α-carboxybenzyloxy)-benzyl]-1,2,3,4-tetrahydro-2-oxoquinoline.

Example 8

A solution of 1 g of 7-ethyl-1,2-dihydro-4-methyl-3-o-nitrobenzyl-2-oxo-1-[2'-(1H-tetrazol-5-yl)-biphenyl-4-ylmethyl]quinoline in 25 ml of ethanol is hydrogenated on 0.3 g of 5% Pd-on-charcoal at 20° and normal pressure until the calculated amount of H$_2$ has been taken up. The catalyst is filtered off, the filtrate is evaporated and the 3-o-aminobenzyl-7-ethyl-1,2-dihydro-4-methyl-2-oxo-1-[2'-(1H-tetrazol-5-yl)biphenyl-4-yl-methyl]quinoline obtained is purified by chromatography.

The following 1-(2'-cyanobiphenyl-4-ylmethyl)-2-oxoquinolines:
3-o-aminobenzyl-7-ethyl-1,2-dihydro-4-methyl-
3-m-amijnobenzyl-7-ethyl-1,2-dihydro-4-methyl-
3-p-aminobenzyl-7-ethyl-1,2-dihydro-4-methyl-
and the following 2-oxo-1-[2'-(1H-tetrazol-5-yl)biphenyl-4-ylmethyl]quinolines:
3-m-aminobenzyl-7-ethyl-1,2-dihydro-4-methyl-
3-p-aminobenzyl-7-ethyl-1,2-dihydro-4-methyl-, m.p. 166°
are obtained analogously by hydrogenation of the corresponding nitro compounds.

Example 9

A solution of 0.3 ml of 36% aqueous HCHO solution, 150 mg of H$_2$SO$_4$, 0.5 ml of water and 5 ml of THF is added dropwise at 10°–30°, with stirring, to a mixture of 483 mg of 3-o-aminobenzyl-1-(2'-cyanobiphenyl-4-ylmethyl-7-ethyl-1,2-dihydro-4-methyl-2-oxoquinoline, 200 mg of NaBH$_4$ and 10 ml of THF. The mixture is stirred for 16 hours at 20°, rendered alkaline with KOH and worked up in conventional manner to give 1-(2'-cyanobiphenyl-4-ylmethyl)-3-o-dimethylaminobenzyl-7-ethyl-1,2-dihydro-4-methyl-2-oxoquinoline.

Example 10

A mixture of 434 mg of 1-(2'-cyanobiphenyl-4-ylmethyl)-7-ethyl-1,2-dihydro-4-methyl-2-oxo-3-(2-oxopropyl)quinoline, 167 mg of O-methylhydroxylamine hydrochloride, 0.16 ml of pyridine and 25 ml of ethanol is stirred for 48 hours at 20°. It is evaporated and worked up in conventional manner to give 1-(2'-cyanobiphenyl-4-ylmethyl)-7-ethyl-1,2-dihydro-4-methyl-3-(2-O-methyloximinopropyl)-2-oxoquinoline.

The following Examples relate to pharmaceutical formulation containing active ingredients of formula I or their salts.

Example A

TABLETS AND COATED TABLETS

Tablets of the following composition are produced by compression in conventional manner and, where required, are provided with a conventional sucrose-based coating:

| | |
|---|---|
| Active ingredient of formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B

HARD GELATIN CAPSULES

Conventional two-part hard gelatin capsules are each filled with

| | |
|---|---|
| Active ingredient of formula I | 100 mg |
| Lactose | 150 mg |
| Cellulose | 50 mg |
| Magnesium stearate | 6 mg |

Example C

SOFT GELATIN CAPSULES

Conventional soft gelatin capsules are filled with a mixture of 50 mg of active ingredient and 250 mg of olive oil in each case.

Example D

AMPOULES

A solution of 200 g of active ingredient in 2 kg of propane-1,2-diol is made up to 10 l with water and filled into ampoules so that each ampoule contains 20 mg of active ingredient.

Example E

AQUEOUS SUSPENSION FOR ORAL ADMINISTRATION

An aqueous suspension is prepared in conventional manner. The unit does (5 ml) contains 100 mg of active ingredient, 100 mg of sodim carboxymethyl cellulose, 5 ml of sodim benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invetion, and without departing from the spriret and scope thereof, can make various changes and modification of the invetion to adapt it to various usages and conditions.

What is claimed is:

1. A 2-oxoquinoline derivative of formula I;

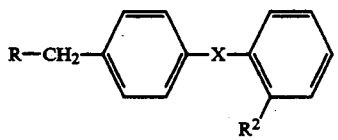

wherein
R is

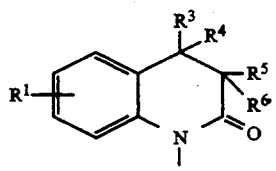

$R^1$ is H, A, OA or SA, $R^2$ is H, COOH, COOA, CN, NO$_2$, NH$_2$, NHCOR$^7$, NHSO$_2$R$^7$ or 1H-tetrazol-5-yl, $R^3$ and $R^4$ are each independently H or A, $R^5$ and $R^6$ are each independently H, A, COOH, COOA, cyanoalkyl, HOOC-alkyl, ACCO-alkyl, H$_2$NCO-alkyl, ANHCO-alkyl, A$_2$NCO-alkyl, cyanoalkenyl, HOOC-alkenyl, ACCO-alkenyl, 1H-tetrazol-5-ylalkyl, 2-oxooxazolidinylalkyl, Ar-alkyl, AO-alkyl, ArO-alkyl, Ar-alkyl-O-alkyl, formylalkyl, oxoalkyl, HOOC-oxoalkyl, ACCO-oxoalkyl, oximinoalkyl, O-alkyloximinoalkyl, HO-alkyl or R$^8$R$^9$N-alkyl, or $R^3$ and $R^5$ together are a bond, $R^7$ is C$_{1-5}$ alkyl, in which one or more H atom(s) are optionally replaced with F, $R^8$ is H or A, $R^9$ is H, A, A—CO, Ar—CO, COOA, CONH$_2$, CONHA, CONHAr, CON(A)$_2$ or CONAAr, X is absent or is —NH—CO—, —CO—NH—, —O—CH(COOH)—, —NH—CH(COOH)—, —NA—CH(COOH)—, —CH=C(COOH)—,
—CH=C(CN)— or —CH=C(1H-tetrazol-5-yl)—, A is C$_{1-16}$ alkyl, Ar is a phenyl group optionally monosubstituted by R$^7$, OR$^7$, Hal, COOH, COOA, CN, NO$_2$, NH$_2$ NHA, N(A)$_2$, NHCOR$^7$, NHSO$_2$R$^7$ or 1H-tetrazol-5-yl, Hal is F, Cl, Br or I, and -alkyl or -alkenyl each independently has up to 6 C atoms or a pharmaceutically acceptable salt thereof.

2. A compound of claim 1, which is
   a) 1,2-Dihydro-2-oxo-1-[2'-(1H-tetrazol-5-yl)biphenyl-4-ylmethyl]quinoline;
   b) 1,2,3,4-tetrahydro-2-oxo-1-[2'-(1H-tetrazol-5-yl)biphenyl-4-ylmethyl]-quinoline;
   c) 7-ethyl-1,2-dihydro-4-methyl-2-oxo-1-[2'-(1H-tetrazol-5-yl) biphenyl-4-ylmethyl]quinoline;
   d) 1,2,3,4-tetrahydro-4,4-dimethyl-2-oxo-1-[2'-( 1H-tetraol-5-yl)biphenyl-4-ylmethyl]quinoline; or
   e) 7-ethyl-1,2,3,4-tetrahydro-4,4-dimethyl-2-oxo-1-[2'-(1H-tetrazol-5-yl)biphenyl-4-ylmethyl]quinoline.

3. A compound of claim 1 wherein A is C$_{1-4}$-alkyl, Hal is F, CL or Br, Ar is unsubstituted phenyl, R is a 1,2-dihydroquinoline or 1,2,3,4-tetrahydroquinoline radical, R$^1$ is H or A, R$^2$ is CN, R$^3$ and R$^4$ are each independently H or methyl, one of R$^5$ R$^6$ is H and the other is H or A, COOH, COOA, cyanolkyl, carboxyalkyl, ACCO-alkyl, carbamoyl-alkyl, N-alkylcarbamoylalkyl, N,N-dialkylcarbamoylalkyl, cyanoalkenyl, carboxyalkenyl, alkoxycarbonylalkenyl, 1H-tetrazol-5-ylalkyl, 2-oxooxazolidinylalkyl, Ar-alkyl, alkoxyalkyl, Ar-oxyalkyl, Ar-alkyloxyalkyl, formylalkyl, oxoalkyl, carboxyoxoalkyl, alkoxycarbonyloxoalkyl, oximinoalkyl, O-alkyloximinoalkyl, hydroxyalkyl, aminoalkyl, alkylaminoalkyl, dialkylaminoalkyl, alkanoylaminoalkyl, aroylaminoalkyl, alkoxycarbonylaminoalkyl, ureidolkyl, alkylureidolkyl, N,N-dialkylureidoalkyl, N-Arureidolkyl, or N-alkyl-N-Ar-ureidolkyl, R$^7$ is CF$_3$ or A, R$^8$ is H, R$^9$ is H, A or A-CO, X is absent, —alkyl is —CH$_2$— or —CH$_2$CH$_2$—and —alkenyl is —CH$_2$—CH$_2$—CH=CH—.

4. A method for the treatment of angiotensin-II dependent hypertension, comprising administering an effective amount of a compound of claim 1.

5. A method for the treatment of angiotensin-II dependent hypertension, comprising administering an effective amount of a compound of claim 1.

UNITED STATES PATENT AND TRADEMARK OFFICE
CERTIFICATE OF CORRECTION

PATENT NO. : 5,371,226
DATED : December 6, 1994
INVENTOR(S) : Werner MEDERSKI et al.

It is certified that error appears in the above-indentified patent and that said Letters Patent is hereby corrected as shown below:

Claim 1; column 15, lines 36, 38 and 41:

Delete "ACCO" and replace with - - AOOC - -  therefor.

Claim 3; column 16, line 31:  Delete "ACCO" and insert

- - AOOC - - .

Claim 3; column 16, lines 43 and 44:  Delete "CH$_2$"

(second occurance).

Signed and Sealed this

Eleventh Day of April, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,371,226
DATED : December 06, 1994
INVENTOR(S) : Werner MEDERSKI et al.

It is certified that error appears in the above-indentified patent and that said Letters Patent is hereby corrected as shown below:

Claim 4; column 16, lines 45-47: Delete claim 4 and replace with - - A pharmaceutical composition, comprising at least one compound of formula I according to claim 1, or physiologically acceptable acid addition salt thereof, and pharmaceutically acceptable carrier - -.

Signed and Sealed this

Fourth Day of March, 1997

*Attest:*

BRUCE LEHMAN

*Attesting Officer*     *Commissioner of Patents and Trademarks*